United States Patent
Krapp et al.

(10) Patent No.: US 9,497,961 B2
(45) Date of Patent: Nov. 22, 2016

(54) COMPOSITION FOR IMPROVING THE EFFICACY OF HERBICIDES

(75) Inventors: Michael Krapp, Altrip (DE); Rainer Berghaus, Speyer (DE); Markus Becker, Meckenheim (DE); Bernd Sievernich, Hassloch (DE); Herve R. Vantieghem, Stutensee (DE)

(73) Assignee: BASF SE, Ludwigshafen (DE)

( * ) Notice: Subject to any disclaimer, the term of this patent is extended or adjusted under 35 U.S.C. 154(b) by 468 days.

(21) Appl. No.: 13/121,285

(22) PCT Filed: Sep. 29, 2009

(86) PCT No.: PCT/EP2009/062598
§ 371 (c)(1),
(2), (4) Date: Mar. 28, 2011

(87) PCT Pub. No.: WO2010/037734
PCT Pub. Date: Apr. 8, 2010

(65) Prior Publication Data
US 2011/0177949 A1    Jul. 21, 2011

(30) Foreign Application Priority Data
Sep. 30, 2008 (EP) .................. 08165527

(51) Int. Cl.
*A01N 25/30* (2006.01)
*A01N 25/02* (2006.01)

(52) U.S. Cl.
CPC ............ *A01N 25/30* (2013.01); *A01N 25/02* (2013.01)

(58) Field of Classification Search
CPC ......... A01N 3/00; A01N 25/02; A01N 25/30
See application file for complete search history.

(56) References Cited

U.S. PATENT DOCUMENTS

| | | | |
|---|---|---|---|
| 4,834,908 A | 5/1989 | Hazen et al. | |
| 5,084,087 A | 1/1992 | Hazen et al. | |
| 5,102,442 A * | 4/1992 | Hazen et al. | 504/110 |
| 6,514,910 B1 * | 2/2003 | Bratz et al. | 504/139 |
| 2011/0177949 A1 | 7/2011 | Krapp et al. | |

FOREIGN PATENT DOCUMENTS

| | | |
|---|---|---|
| EP | 0 394 847 | 10/1990 |
| WO | WO 00/53014 | 9/2000 |
| WO | WO 0217721 | 3/2002 |
| WO | WO 2006/050141 | 5/2006 |
| WO | WO 2007039215 | 4/2007 |
| WO | WO 2007/065026 | 6/2007 |

OTHER PUBLICATIONS

Database Caplus [Online] Chemical Abstracts Service, Columbus, Ohio, US; Oct. 23, 1996, R. S. Tann et al.: "Effect of various chain length methyl esters as agricultural tank mix adjuvants" XP002608684 found in STN Accession No. 1996:627973, Database Accession No. 1996:627973, R.S. Tann et al.: "Effect of various carbon chain length metyl esters as agricultural tank mix adjuvants" FRI Bulletin, Ed. 193, No. Prov. of 4$^{th}$ Int. Symp. on adjuvants., 1995, p. 72-77.
F. Cabanne et al.: "Influence of alkyl oleates on efficacy of phenmedipham applied as an acetone: water solution on Galium aparine." Weed Research, Ed. 39, 1999, p. 57-67, XP002608685.
International Preliminary Report on Patentability for PCT/EP2009/062598.
Notice of Opposition, issued in corresponding European Patent No. 2346321, dated Oct. 28, 2015.
Knothe, "Dependence of Biodiesel Fuel Properties on the Structure of Fatty Acid Alkyl Esters," Fuel Processing Technology, vol. 86, (2005), pp. 1059-1070.

* cited by examiner

*Primary Examiner* — Johann R Richter
*Assistant Examiner* — Danielle Sullivan
(74) *Attorney, Agent, or Firm* — Brinks Gilson & Lione

(57) ABSTRACT

The present invention relates to a novel composition for improving the effectiveness of herbicides, to the use of this composition for improving the effectiveness of herbicides, to a herbicidal agent which comprises this composition and at least one herbicide, and to the use of this herbicidal agent for controlling undesired plant growth. The composition comprises:
(a) at least one $C_1$-$C_4$-alkyl ester of at least one aliphatic $C_{14}$-$C_{22}$-carboxylic acid, where the at least one carboxylic acid consists to at least 70% by weight of aliphatic carboxylic acids having 18 carbon atoms;
(b) at least one anionic surfactant which is selected from the esterification products of monohydroxy-functional alkyl polyethers with inorganic polyprotonic acids;
(c) at least one aliphatic $C_{14}$-$C_{22}$-carboxylic acid;
(d) optionally at least one antifoam; and
(e) at least one aromatic solvent.

13 Claims, No Drawings

COMPOSITION FOR IMPROVING THE EFFICACY OF HERBICIDES

This application is a National Stage application of International Application No. PCT/EP2009/062598 filed Sep. 29, 2009, the entire contents of which is hereby incorporated herein by reference. This application also claims priority under 35 U.S.C. § 119 to European Patent Application No. 08165527.6 filed Sep. 30, 2008, the entire contents of which is hereby incorporated herein by reference.

The present invention relates to a novel composition for improving the effectiveness of herbicides, to the use of this composition for improving the effectiveness of herbicides, to a herbicidal agent which comprises this composition and at least one herbicide, and to the use of this herbicidal agent for controlling undesired plant growth.

It is generally known that both the uptake and also the effectiveness of many pesticides, such as, for example, herbicides, can be improved by adding adjuvants, so-called boosters. The action mechanism of these additives is complex and cannot merely be attributed to adapted surface properties of the leaf surface.

WO 00/53014 describes a herbicidal composition with improved effectiveness which, besides a herbicide of the topramezone type, comprises an adjuvant as action improver. This comprises a $C_1$-$C_5$-alkyl $C_5$-$C_{22}$-alkanoate, a $C_{10}$-$C_{20}$-carboxylic acid, a partial phosphoric or sulfuric acid ester of a monohydroxy-functional polyalkyl ether and optionally an alkyl polyoxyalkylene polyether. Preferred $C_1$-$C_5$-alkyl $C_5$-$C_{22}$-alkanoates are methyl oleate, methyl palmitate and ethyl oleate and mixtures thereof. Specifically, the $C_1$-$C_5$-alkyl $C_5$-$C_{22}$-alkanoate used is a 1:1 mixture of methyl oleate and methyl palmitate.

Such action improver systems are commercially available under the name DASH®, e.g. DASH® HC, from BASF Corporation, USA.

A disadvantage of this action improver system is that at relatively low temperatures, sometimes even at 10° C., and/or upon prolonged storage, it precipitates and becomes solid. Since the action improver system is generally mixed in the spray tank with the herbicide, precipitation hinders the dispersibility of the action improver in the tank mix, and the product is no longer applied to the plants in a uniform concentration. To ensure good dispersion, the action improver must first be heated in order to dissolve it, which naturally makes its handling enormously difficult.

It was therefore an object of the present invention to provide an action improver system which forms precipitates neither at low temperatures, e.g. at or below 10° C., but in particular also at or below 0° C., e.g. at or below −5° C., nor upon prolonged storage, and is thus easier to handle.

The inventors of the present application have found that the precipitate formation is attributed to the alkyl alkanoate constituent and that this can be prevented if the alkyl alkanoate has a certain composition.

The object is therefore achieved by a composition comprising:
(a) at least one $C_1$-$C_4$-alkyl ester of at least one aliphatic $C_{14}$-$C_{22}$-carboxylic acid, where the at least one carboxylic acid consists to at least 70% by weight of aliphatic carboxylic acids having 18 carbon atoms;
(b) at least one anionic surfactant which is selected from the esterification products of monohydroxy-functional alkyl polyethers with inorganic polyprotonic acids;
(c) at least one aliphatic $C_{14}$-$C_{22}$-carboxylic acid;
(d) optionally at least one antifoam; and
(e) at least one aromatic solvent.

Within the context of the present invention, generic names of radicals have the following meanings:

Within the context of the present invention, halogen is fluorine, chlorine or bromine.

$C_1$-$C_4$-Alkyl is a linear or branched alkyl radical having 1 to 4 carbon atoms. Examples thereof are methyl, ethyl, propyl, isopropyl, n-butyl, sec-butyl, isobutyl and tert-butyl.

$C_1$-$C_6$-Alkyl is a linear or branched alkyl radical having 1 to 6 carbon atoms. Examples thereof are methyl, ethyl, propyl, isopropyl, n-butyl, sec-butyl, isobutyl, tert-butyl, pentyl, isopentyl, neopentyl, hexyl, isohexyl and positional isomers thereof.

$C_1$-$C_{10}$-Alkyl is a linear or branched alkyl radical having 1 to 10 carbon atoms. Besides the examples already specified for $C_1$-$C_6$-alkyl, examples thereof are heptyl, octyl, 2-ethylhexyl, nonyl and decyl and also positional isomers thereof.

$C_1$-$C_6$-Haloalkyl is a $C_1$-$C_6$-alkyl radical in which at least one hydrogen atom is replaced by a halogen atom, e.g. by F, Cl or Br. Preferably, $C_1$-$C_6$-haloalkyl is $C_1$-$C_4$-haloalkyl, i.e. is a $C_1$-$C_4$-alkyl radical in which at least one hydrogen atom is replaced by a halogen atom, e.g. by F, Cl or Br. Examples thereof are chloromethyl, dichloromethyl, trichloromethyl, fluoromethyl, difluoromethyl, trifluoromethyl, 1,1-difluoroethyl, 2,2,2-trifluoroethyl, pentafluoroethyl, 3,3,3-trifluoropropyl, 1,1-dichloroethyl, 2,2,2-trichloroethyl, pentachloroethyl, 3,3,3-trichloropropyl and the like.

$C_1$-$C_6$-Alkoxy is a $C_1$-$C_6$-alkyl radical which is bonded via an oxygen atom. Examples thereof are methoxy, ethoxy, propoxy, isopropoxy, n-butoxy, 2-butoxy, isobutoxy, tert-butoxy, pentoxy and hexoxy and positional isomers thereof.

$C_1$-$C_6$-Haloalkoxy is a $C_1$-$C_6$-haloalkyl radical which is bonded via an oxygen atom. Examples thereof are chloromethoxy, dichloromethoxy, trichloromethoxy, fluoromethoxy, difluoromethoxy, trifluoromethoxy, 1,1-difluoroethoxy, 2,2,2-trifluoroethoxy, pentafluoroethoxy, 3,3,3-trifluoropropoxy, 1,1-dichloroethoxy, 2,2,2-trichloroethoxy, pentachloroethoxy, 3,3,3-trichloropropoxy and the like.

$C_1$-$C_6$-Alkylthio is a $C_1$-$C_6$-alkyl radical which is bonded via a sulfur atom. Examples thereof are methylthio, ethylthio, propylthio, isopropylthio, n-butylthio, 2-butylthio, isobutylthio, tert-butylthio, pentylthio and hexylthio, and positional isomers thereof.

$C_1$-$C_6$-Haloalkylthio is a $C_1$-$C_6$-haloalkyl radical which is bonded via a sulfur atom. Examples thereof are chloromethylthio, dichloromethylthio, trichloromethylthio, fluoromethylthio, difluoromethylthio, trifluoromethylthio, 1,1-difluoroethylthio, 2,2,2-trifluoroethylthio, pentafluoroethylthio, 3,3,3-trifluoropropylthio, 1,1-dichloroethylthio, 2,2,2-trichloroethylthio, pentachloroethylthio, 3,3,3-trichloropropylthio and the like.

$C_1$-$C_6$-Alkylsulfinyl is a $C_1$-$C_6$-alkyl radical which is bonded via an SO group. Examples thereof are methylsulfinyl, ethylsulfinyl, propylsulfinyl, isopropylsulfinyl, n-butylsulfinyl, 2-butylsulfinyl, isobutylsulfinyl, tert-butylsulfinyl, pentylsulfinyl and hexylsulfinyl and also positional isomers thereof.

$C_1$-$C_6$-Haloalkylsulfinyl is a $C_1$-$C_6$-haloalkyl radical which is bonded via an SO group. Examples thereof are chloromethylsulfinyl, dichloromethylsulfinyl, trichloromethylsulfinyl, fluoromethylsulfinyl, difluoromethylsulfinyl, trifluoromethylsulfinyl, 1,1-difluoroethylsulfinyl, 2,2,2-trifluoroethylsulfinyl, pentafluoroethylsulfinyl, 3,3,3-trifluoropropylsulfinyl, 1,1-dichloroethylsulfinyl, 2,2,2-trichloroethylsulfinyl, pentachloroethylsulfinyl, 3,3,3-trichloropropylsulfinyl and the like.

$C_1$-$C_6$-Alkylsulfonyl is a $C_1$-$C_6$-alkyl radical which is bonded via an $SO_2$ group. Examples thereof are methylsulfonyl, ethylsulfonyl, propylsulfonyl, isopropylsulfonyl, n-butylsulfonyl, 2-butylsulfonyl, isobutylsulfonyl, tert-butylsulfonyl, pentylsulfonyl and hexylsulfonyl and also positional isomers thereof.

$C_1$-$C_6$-Haloalkylsulfonyl is a $C_1$-$C_6$-haloalkyl radical which is bonded via an $SO_2$ group. Examples thereof are chloromethylsulfonyl, dichloromethylsulfonyl, trichloromethylsulfonyl, fluoromethylsulfonyl, difluoromethylsulfonyl, trifluoromethylsulfonyl, 1,1-difluoroethylsulfonyl, 2,2,2-trifluoroethylsulfonyl, pentafluoroethylsulfonyl, 3,3,3-trifluoropropylsulfonyl, 1,1-dichloroethylsulfonyl, 2,2,2-trichloroethylsulfonyl, pentachloroethylsulfonyl, 3,3,3-trichloropropylsulfonyl and the like.

Aliphatic $C_{14}$-$C_{22}$-carboxylic acids are monocarboxylic acids of the formula R—COOH, in which R is an aliphatic radical having 13 to 21 carbon atoms. The aliphatic radical may be $C_{13}$-$C_{21}$-alkyl, $C_{13}$-$C_{21}$-alkenyl, $C_{13}$-$C_{21}$-alkadienyl, $C_{13}$-$C_{21}$-alkatrienyl, $C_{13}$-$C_{21}$-alkatetraenyl, $C_{13}$-$C_{21}$-alkapentaenyl, $C_{13}$-$C_{21}$-alkahexaenyl or $C_{13}$-$C_{21}$-alkynyl. If the aliphatic radical is an alkyl radical, the aliphatic carboxylic acid is a saturated carboxylic acid; if the aliphatic radical is an alkenyl radical, then the aliphatic carboxylic acid is a monounsaturated carboxylic acid; if the aliphatic radical is an alkadienyl radical, then the aliphatic carboxylic acid is a diunsaturated carboxylic acid; if the aliphatic radical is an alkatrienyl radical, then the aliphatic carboxylic acid is a triunsaturated carboxylic acid; if the aliphatic radical is an alkatetraenyl radical, then the aliphatic carboxylic acid is a tetraunsaturated carboxylic acid; if the aliphatic radical is an alkapentaenyl radical, then the aliphatic carboxylic acid is a pentaunsaturated carboxylic acid; and if the aliphatic radical is an alkahexaenyl radical, then the aliphatic carboxylic acid is a hexaunsaturated carboxylic acid. The aliphatic radical may be linear or branched; however, it is preferably unbranched (linear). The aliphatic $C_{14}$-$C_{22}$-carboxylic acids may be of natural origin or synthetic. Examples of naturally occurring aliphatic $C_{14}$-$C_{22}$-carboxylic acids are myristic acid, pentadecanoic acid, palmitic acid, margaric acid, stearic acid, nonadecanoic acid, arachic acid, behenic acid (saturated, unbranched fatty acids), palmitoleic acid, oleic acid, erucic acid (monounsaturated, unbranched fatty acids), linoleic acid, (diunsaturated, unbranched fatty acid), linolenic acid, elaeostearic acid (triunsaturated, unbranched fatty acids), arachidonic acid (tetraunsaturated, unbranched fatty acid), clupanodonic acid (pentaunsaturated, unbranched fatty acid) and docosahexaenoic acid (hexaunsaturated, unbranched fatty acid).

$C_2$-$C_4$-Alkylene oxides are epoxide compounds of $C_2$-$C_4$-alkenes. Examples are ethylene oxide, propylene oxide and butylene oxide.

$C_{16}$-$C_{20}$-Alkanols are alkanes having 16 to 20 carbon atoms in which a hydrogen atom is replaced by an OH group. Examples are hexadecanol, heptadecanol, octadecanol, nonadecanol, eicosanol and the positional isomers thereof.

$C_{10}$-$C_{20}$-Alkanols are alkanes having 10 to 20 carbon atoms in which a hydrogen atom is replaced by an OH group. Besides the compounds specified previously for $C_{16}$-$C_{20}$-alkanols, examples are decanol, 2-propylheptanol, undecanol, dodecanol, tridecanol, tetradecanol, pentadecanol and the positional isomers thereof.

$C_1$-$C_{20}$-Alkanols are alkanes having 1 to 20 carbon atoms in which a hydrogen atom is replaced by an OH group. Besides the compounds specified previously for $C_{10}$-$C_{20}$-alkanols, examples are methanol, ethanol, propanol, isopropanol, butanol, sec-butanol, isobutanol, tert-butanol, pentanol, hexanol, heptanol, octanol, 2-ethylhexanol, nonanol and the positional isomers thereof.

The details given below regarding preferred features of the compositions according to the invention and their use apply both on their own taken by themselves and also in particular in any conceivable combination with one another.

According to the invention, the at least one aliphatic $C_{14}$-$C_{22}$-carboxylic acid of component (a) consists to at least 70% by weight, e.g. to 70 to 98% by weight, preferably 70 to 95% by weight or 70 to 92% by weight, of aliphatic carboxylic acids having 18 carbon atoms. This means that the at least one aliphatic $C_{14}$-$C_{22}$-carboxylic acid comprises 0 to 30% by weight of $C_{14}$-$C_{17}$- and/or $C_{19}$-$C_{22}$-carboxylic acids, based on the total weight of all aliphatic $C_{14}$-$C_{22}$-carboxylic acids of component (a). In one preferred embodiment of the invention, the at least one aliphatic $C_{14}$-$C_{22}$-carboxylic acid of component (a) consists to at least 75% by weight, e.g. to 75 to 98% by weight, preferably 75 to 95% by weight or 75 to 92% by weight, particularly preferably to at least 80% by weight, e.g. to 80 to 98% by weight, preferably 80 to 95% by weight or 80 to 92% by weight; more preferably to at least 85% by weight, e.g. to 85 to 98% by weight, preferably 85 to 95% by weight or 85 to 92% by weight; and in particular to at least 90% by weight, e.g. to 90 to 98% by weight, preferably 90 to 95% by weight or 90 to 92% by weight, of aliphatic carboxylic acids having 18 carbon atoms.

Preferably, component (a) comprises at least 70% by weight, e.g. 70 to 98% by weight, preferably 70 to 95% by weight or 70 to 92% by weight; particularly preferably at least 75% by weight, e.g. 75 to 98% by weight, preferably 75 to 95% by weight or 75 to 92% by weight; more preferably at least 80% by weight, e.g. 80 to 98% by weight, preferably 80 to 95% by weight or 80 to 92% by weight; even more preferably at least 85% by weight, e.g. to 85 to 98% by weight, preferably 85 to 95% by weight or 85 to 92% by weight; and in particular at least 90% by weight, e.g. to 90 to 98% by weight, preferably 90 to 95% by weight or 90 to 92% by weight, of at least one $C_1$-$C_4$-alkyl ester of at least one aliphatic $C_{18}$-carboxylic acid, based on the total weight of all $C_1$-$C_4$-alkyl esters of the at least one aliphatic $C_{14}$-$C_{22}$-carboxylic acid of component (a).

The $C_1$-$C_4$-alkyl ester of component (a) is preferably the methyl or ethyl ester or mixtures thereof and in particular the methyl ester.

The aliphatic carboxylic acids having 18 carbon atoms of component (a) are preferably selected from saturated $C_{18}$-carboxylic acids, monounsaturated $C_{18}$-carboxylic acids, diunsaturated $C_{18}$-carboxylic acids, triunsaturated $C_{18}$-carboxylic acids and mixtures thereof. Particularly preferably, the aliphatic carboxylic acids having 18 carbon atoms of component (a) are a mixture of at least one saturated $C_{18}$-carboxylic acid, at least one monounsaturated $C_{18}$-carboxylic acid, at least one diunsaturated $C_{18}$-carboxylic acid and at least one triunsaturated $C_{18}$-carboxylic acid.

In this connection, it is preferred for the mixture of the $C_{18}$-carboxylic acids to comprise the at least one monounsaturated $C_{18}$-carboxylic acid in an amount of at least 60% by weight, preferably of at least 65% by weight, in particular of at least 70% by weight, e.g. from 60 to 95% by weight, or 65 to 95% by weight, or 70 to 95% by weight, preferably 70 to 90% by weight; particularly preferably 70 to 85% by weight and in particular 70 to 80% by weight; particularly preferably of at least 75% by weight, e.g. from 75 to 95% by weight, preferably 75 to 90% by weight, particularly preferably 75 to 85% by weight and in particular 75 to 80% by weight; and in particular at least of 78% by weight, e.g. from 78 to 95% by weight, preferably 78 to 90% by weight, particularly preferably 78 to 85% by weight and in particular 78 to 80% by weight; based on the total weight of the mixture, the total amount of $C_{18}$-carboxylic acids being at least 70% by weight, e.g. 70 to 98% by weight, preferably 75 to 95% by weight.

The at least one diunsaturated $C_{18}$-carboxylic acid is present in the mixture of the $C_{18}$-carboxylic acids preferably in an amount of at least 10% by weight, e.g. from 10 to 20% by weight, preferably 10 to 18% by weight and in particular 10 to 16% by weight; particularly preferably of at least 15% by weight, e.g. from 15 to 20% by weight, preferably 15 to 18% by weight and in particular 15 to 16% by weight; based on the total weight of the mixture.

The at least one triunsaturated $C_{18}$-carboxylic acid is present in the mixture of the $C_{18}$-carboxylic acids preferably in an amount of from 2 to 6% by weight, particularly preferably 3 to 5% by weight and in particular of about 4% by weight, based on the total weight of the mixture.

The at least one saturated $C_{18}$-carboxylic acid is present in the mixture of the $C_{18}$-carboxylic acids preferably in an amount of from 0.8 to 4% by weight, particularly preferably 1 to 2% by weight, based on the total weight of the mixture.

Preferably, the at least one monounsaturated $C_{18}$-carboxylic acid comprises oleic acid. Here, the at least one monounsaturated $C_{18}$-carboxylic acid consists particularly to at least 90% by weight, particularly preferably to at least 95% by weight and in particular to at least 98% by weight, of oleic acid.

The at least one saturated $C_{18}$-carboxylic acid preferably comprises stearic acid. Here, the at least one saturated $C_{18}$-carboxylic acid particularly consists to at least 90% by weight, particularly preferably to at least 95% by weight and in particular to at least 98% by weight, of stearic acid.

Preferably, the at least one diunsaturated $C_{18}$-carboxylic acid comprises linoleic acid. Here, the at least one diunsaturated $C_{18}$-carboxylic acid particularly consists to at least 90% by weight, particularly preferably to at least 95% by weight and in particular to at least 98% by weight, of linoleic acid.

Preferably, the at least one triunsaturated $C_{18}$-carboxylic acid comprises linolenic acid and/or elaeostearic acid. Here, the at least one triunsaturated $C_{18}$-carboxylic acid particularly consists to at least 90% by weight, particularly preferably to at least 95% by weight and in particular to at least 98% by weight, of linolenic acid and/or elaeostearic acid.

Besides the at least one $C_1$-$C_4$-alkyl ester of the at least one aliphatic $C_{18}$-carboxylic acid, the component (a) comprises preferably also at least one $C_1$-$C_4$-alkyl ester of at least one aliphatic $C_{14}$- and/or $C_{16}$-carboxylic acid. The $C_1$-$C_4$-alkyl ester is preferably the methyl or ethyl ester or mixtures thereof and in particular the methyl ester. The $C_{14}$-carboxylic acid is preferably myristic acid. The $C_{16}$-carboxylic acid is preferably palmitic acid, palmitoleic acid or a mixture thereof. Preferably, component (a) comprises these esters in an amount of at most 20% by weight, e.g. from 1 to 20% by weight or preferably 5 to 20% by weight; particularly preferably at most 15% by weight, e.g. from 1 to 15% by weight or preferably 5 to 15% by weight; and in particular of at most 10% by weight, e.g. from 1 to 10% by weight or preferably 5 to 10% by weight; based on the total weight of all $C_1$-$C_4$-alkyl esters of the at least one aliphatic $C_{14}$-$C_{22}$-carboxylic acid.

$C_1$-$C_4$-Alkyl esters of aliphatic $C_{14}$-$C_{22}$-carboxylic acids which have the inventive and preferred features are commercially available, for example under the name Edenor® ME Ti 05 (or Synative® ES ME Ti 05) from Cognis. Within the context of the present invention, this product is particularly preferably used as component (a).

In the at least one anionic surfactant of component (b), the ester is generally a partial ester (also half-ester below), this means the polyprotonic inorganic acid is only partially esterified. The inorganic polyprotonic acid is usually a polyprotonic oxoacid which is preferably selected from sulfuric acid and phosphoric acid; it is particularly preferably phosphoric acid. The esters in the case of sulfuric acid are generally half-esters (i.e. only one proton or one OH group of the sulfuric acid is esterified); also the phosphoric acid is preferably only partially esterified and component (b) is the mono- or diester or in particular a mixture of mono- and diesters of phosphoric acid. As a consequence of the production, the anionic surfactant can also comprise certain fractions of completely esterified product. In this case, the completely esterified product generally constitutes not more than 50% by weight, in particular not more than 30% by weight, based on the amount of component (b) used.

The esters are generally obtainable by reacting monohydroxy-functional alkyl polyethers (polyoxyalkylene ethers) with the polyprotonic inorganic acid or a suitable derivative thereof, e.g. with its chloride, e.g. with sulfuric acid, phosphoric acid or POCl$_3$; preferably in a stoichiometry or under conditions such that the acid is only partially esterified. The monohydroxy-functional alkyl polyethers used are generally commercially available. They are obtainable, for example, by oxyalkylation, in particular ox-$C_2$-$C_4$-alkylation of alkanols, preferably of $C_1$-$C_{40}$-alkanols and preferably of long-chain alkanols, preferably of $C_{10}$-$C_{30}$- and in particular of $C_{10}$-$C_{20}$-alkanols, with alkylene oxides, preferably with $C_2$-$C_4$-alkylene oxides, such as ethylene oxide, propylene oxide, butylene oxide or mixtures thereof, in particular with ethylene oxide or a mixture of ethylene oxide and propylene oxide and specifically with ethylene oxide. Preferred monohydroxy-functional alkyl polyethers have a molecular weight of from 400 to 3000 and in particular from 600 to 1200. They are particularly preferably obtainable by reaction with 5 to 20, in particular 10 to 15 mol of ethylene oxide and optionally 1 to 10, preferably 2 to 6 mol of propylene oxide, per mole of alkanol.

The at least one anionic surfactant is particularly preferably selected from phosphoric acid partial esters of at least one monohydroxy-functional alkyl polyether. That stated above applies with regard to suitable and preferred monohydroxy-functional alkyl polyethers.

The anionic surfactants are generally used in the form of their salts, in particular in the form of their alkali metal salts, ammonium salts or substituted ammonium salts. Substituted ammonium salts are understood as meaning the salts of primary, secondary or tertiary alkyl- or hydroxyalkylamines. Preference is given to the alkali metal salts, in particular the sodium and potassium salts and also the ammonium salts ($NH_4^+$ salts).

In particular, commercially available products such as Klearfac® AA 270 from BASF Corporation, Mt. Olive, N.J., USA or Lutensit® A-EP from BASF SE are used. Lutensit® A-EP is more preferred here. In both cases these are the sodium salts of phosphoric acid mono- and diesters of monohydroxy-functional alkyl polyethers based on ethoxylated or ethoxylated-co-propoxylated alkanols.

The at least one aliphatic $C_{14}$-$C_{22}$-carboxylic acid of component (c) may either be synthetic carboxylic acids or those of natural origin. It is preferably those of natural origin.

The carboxylic acid may be saturated or mono- or polyunsaturated. It may also be a mixture of different acids. Examples of suitable carboxylic acids are myristic acid, pentadecanoic acid, palmitic acid, margaric acid, stearic acid, nonadecanoic acid, arachic acid, behenic acid (saturated, unbranched fatty acids), palmitoleic acid, oleic acid, erucic acid (monounsaturated, unbranched fatty acids), linoleic acid (diunsaturated, unbranched fatty acids), linolenic acid, elaeostearic acid (triunsaturated, unbranched fatty acids), arachidonic acid (tetraunsaturated, unbranched fatty acid), clupanodonic acid (pentaunsaturated, unbranched fatty acid) and docosahexaenoic acid (hexaunsaturated, unbranched fatty acid). The at least one aliphatic $C_{14}$-$C_{22}$-carboxylic acid preferably comprises oleic acid. Preferably, the fraction of oleic acid here is at least 80% by weight, particularly preferably at least 85% by weight, more preferably at least 90% by weight, even more preferably at least 95% by weight and in particular at least 98% by weight, based on the total weight of all aliphatic $C_{14}$-$C_{22}$-carboxylic acids of component (c). Specifically, the at least one aliphatic $C_{14}$-$C_{22}$-carboxylic acid is oleic acid; i.e. the fraction of different constituents which may be present arises for technical reasons and is below 2% by weight and in most cases even below 1% by weight.

The at least one antifoam (d) optionally present in the booster composition according to the invention prevents the formation of foam and is preferably selected from customary antifoams for crop protection formulations. Of suitability are, for example, antifoams based on siloxane (e.g. Silikon® SRE from Wacker or Rhodorsil® from Rhodia), long-chain alcohols, fatty acids and fatty acid salts, e.g. magnesium stearate. The antifoam is preferably one based on siloxane, in particular a trimethylsiloxane such as Silikon® SRE from Wacker.

The composition according to the invention preferably comprises at least one antifoam (d).

Suitable aromatic solvents are in particular alkyl-substituted aromatics, such as toluene, the xylenes, ethylbenzenes and benzenes with relatively long-chain alkyl radicals, e.g. $C_9$-$C_{10}$-dialkyl- and trialkylbenzenes (e.g. available under the name Solvesso® 100 from Exxon Mobile Europe or Aromatic 100 from Exxon Mobile USA), $C_{10}$-$C_{11}$-alkylbenzenes (e.g. available under the name Solvesso® 150 from Exxon Mobile Europe or Aromatic 150 from Exxon Mobile USA) and alkylnaphthalenes (e.g. available under the name Solvesso® 200 from Exxon Mobile Europe or Aromatic 200 from Exxon Mobile USA). Mixtures of the aforementioned aromatics are also suitable. Among these, preference is given to the benzenes substituted with higher alkyl radicals, such as $C_9$-$C_{10}$-dialkyl- and trialkylbenzenes and in particular $C_{10}$-$C_{11}$-alkylbenzenes (Solvesso® or Aromatic 100 and in particular 150).

The at least one aromatic solvent particularly preferably comprises at most 5% by weight, more preferably at most 2% by weight and in particular at most 1% by weight, based on the total weight of the aromatic solvent, of naphthalene. Such solvents with at most 1% by weight naphthalene content are commercially available, for example, from Exxon Mobile Europe with the designation ND (naphthalene depleted), for example Solvesso® 150 ND and Solvesso® 200 ND from Exxon Mobile Europe. Yet smaller naphthalene contents of at most 0.1% by weight are present in the products Aromatic 150 ULN and Aromatic 200 ULN from Exxon Mobile USA. Specifically, Solvesso® 150 ND is used as component (e).

The components (a) to (e) are preferably present in the composition according to the invention in the following amounts:
(a) 5 to 90% by weight, based on the total weight of components (a), (b), (c), (d) and (e);
(b) 4 to 40% by weight, based on the total weight of components (a), (b), (c), (d) and (e);
(c) 2 to 40% by weight, based on the total weight of components (a), (b), (c), (d) and (e);
(d) 0 to 0.5% by weight, e.g. 0.005 to 0.1% by weight, based on the total weight of components (a), (b), (c), (d) and (e);
(e) ad 100% by weight, based on the total weight of components (a), (b), (c), (d) and (e).

The components (a) to (e) are particularly preferably present in the following amounts:
(a) 20 to 60% by weight, based on the total weight of components (a), (b), (c), (d) and (e);
(b) 10 to 40% by weight, based on the total weight of components (a), (b), (c), (d) and (e);
(c) 2 to 15% by weight, based on the total weight of components (a), (b), (c), (d) and (e);
(d) 0 to 0.5% by weight, e.g. 0.005 to 0.1% by weight, based on the total weight of components (a), (b), (c), (d) and (e);
(e) ad 100% by weight, based on the total weight of components (a), (b), (c), (d) and (e).

The components (a) to (e) are more preferably present in the following amounts:
(a) 25 to 45% by weight, based on the total weight of components (a), (b), (c), (d) and (e);
(b) 15 to 30% by weight, based on the total weight of components (a), (b), (c), (d) and (e);
(c) 2 to 10% by weight, based on the total weight of components (a), (b), (c), (d) and (e);
(d) 0 to 0.5% by weight, e.g. 0.005 to 0.1% by weight, based on the total weight of components (a), (b), (c), (d) and (e);
(e) ad 100% by weight, based on the total weight of components (a), (b), (c), (d) and (e).

In particular, the components (a) to (e) are present in the following amounts:
(a) 35 to 40% by weight, based on the total weight of components (a), (b), (c), (d) and (e);
(b) 20 to 25% by weight, based on the total weight of components (a), (b), (c), (d) and (e);
(c) 3 to 7% by weight, based on the total weight of components (a), (b), (c), (d) and (e);
(d) 0 to 0.5% by weight, e.g. 0.005 to 0.1% by weight, based on the total weight of components (a), (b), (c), (d) and (e);
(e) ad 100% by weight, based on the total weight of components (a), (b), (c), (d) and (e).

Specifically, the components (a) to (e) are present in the following amounts:
(a) 35 to 40% by weight, more specifically 37.5% by weight, based on the total weight of the components (a), (b), (c), (d) and (e); the $C_1$-$C_4$-alkyl ester of the at least one aliphatic $C_{14}$-$C_{22}$-carboxylic acid used here is specifically Edenor® Me Ti 05 from Cognis which comprises at least 65% by weight of methyl oleate;
(b) 20 to 25% by weight, more specifically 22.5% by weight, based on the total weight of the components (a), (b), (c), (d) and (e); the anionic surfactant used here is specifically Lutensit® A-EP from BASF SE;
(c) 3 to 7% by weight, more specifically 5% by weight, based on the total weight of the components (a), (b), (c), (d) and (e); the aliphatic $C_{14}$-$C_{22}$-carboxylic acid used here is specifically oleic acid;
(d) 0.005 to 0.1% by weight, more specifically 0.03% by weight, based on the total weight of the component (a), (b), (c), (d) and (e); the antifoam used here is specifically a siloxane antifoam, such as Silikon® SRE from Wacker;

(e) ad 100% by weight, based on the total weight of the components (a), (b), (c), (d) and (e); the solvent used here is specifically Solvesso® 150 ND from Exxon.

The composition according to the invention improves the effect of herbicides when it is applied together with these, i.e. in a time and locality context.

The invention therefore further provides the use of the above-described composition according to the invention for improving the effect of herbicides. With regard to the way in which the composition according to the invention is used and suitable and preferred herbicides, reference is made to the following explanations regarding the herbicidal agent.

The invention further provides a herbicidal agent comprising (A) a composition improving the effect of herbicides (also called booster composition) according to the above definition; and (B) at least one herbicide.

With regard to suitable and preferred embodiments of the booster composition, reference is made to the details above.

The agent according to the invention may be a physical mixture of the composition A with the at least one herbicide B. Accordingly, the invention also provides a mixture which comprises the composition A and at least one herbicide B. The agent can, however, also be any desired combination of the composition A with at least one herbicide B, where A and B must not be formulated together.

One example of an agent according to the invention in which the composition A and the at least one herbicide B are not formulated together is a two-component kit. Accordingly, the present invention also provides a two-component kit comprising a first component which comprises the composition A, and a second component which comprises at least one herbicide B, a liquid or solid carrier and optionally at least one interface-active substance and/or at least one customary auxiliary. Suitable liquid and solid carriers, interface-active substances and customary auxiliaries are described below.

Suitable herbicides are in principle all customary herbicides. These include:

b1) from the group of lipid biosynthesis inhibitors:

these are compounds which inhibit lipid biosynthesis. This inhibition may be based on an inhibition of the acetyl CoA carboxylase (also referred to hereinbelow as ACC herbicides) or on another mechanism (also reffered to hereinbelow as non-ACC herbicides). The ACC herbicides belong to group A of the HRAC classification, whereas the non-ACC herbicides belong to group N of the HRAC classification.

Examples are:

ACC herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim and tralkoxydim, and also non-ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of ALS inhibitors:

these are compounds whose herbicidal effect is based on the inhibition of the acetolactate synthase and thus on the inhibition of the biosynthesis of branched-chain amino acids. Such inhibitors belong to group B of the HRAC classification. Examples are:

sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, mesosulfuron, metsulfuron, metsulfuron-methyl, nicosulfuron, orthosulfamuron, oxasulfuron, primisulfuron, primisulfuron-methyl, prosulfuron, pyrazosulfuron, pyrazosulfuron-ethyl, rimsulfuron, suifometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimdinyl benzoates such as bispyribac, bispyribac-sodium, pyribenzoxim, pyriftalid, pyriminobac, pyriminobac-methyl, pyrithiobac, pyrithiobac-sodium, and sulfonylaminocarbonyltriazolinone herbicides such as flucarbazone, flucarbazone-sodium, propoxycarbazone, propoxycarbazone-sodium, thiencarbazone and thiencarbazone-methyl. Among these, compositions which comprise at least one imidazolinone herbicide constitute a preferred embodiment of the invention;

b3) from the group of photosynthesis inhibitors:

these are compounds whose herbicidal effect is based on the inhibition of photosystem II in plants (so-called PSII inhibitors, groups C1, C2 and C3 of the HRAC classification) or on the hindrance of electron transfer in photosystem I of the plants (so-called PSI inhibitors, group D of the HRAC classification) and thus on an inhibition or interference in the photosynthesis. Among these, PSII inhibitors are preferred. Examples are:

amicarbazone, inhibitors of photosystem II, e.g. triazine herbicides, including chlorotriazines, triazinones, triazinediones, methylthiotriazines and pyridazinones such as ametryn, atrazine, chloridazon, cyanazine, desmetryn, dimethametryn, hexazinone, metribuzin, prometon, prometryn, propazine, simazine, simetryn, terbumeton, terbuthylazine, terbutryn and trietazine, arylureas such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thidiazuron, phenyl carbamates such as desmedipham, carbutylate, phenmedipham, phenmedipham-ethyl, nitrile herbicides such as bromofenoxim, bromoxynil and its salts and esters, ioxynil and its salts and esters, uracils such as bromacil, lenacil and terbacil, and also bentazone and bentazone-sodium, pyridatre, pyridafol, pentanochlor and propanil and inhibitors of photosystem I such as diquat, diquat-dibromide, paraquat, paraquat-dichloride and paraquat-dimetilsulfate. Among these, compositions which comprise at least one arylurea herbicide constitute a preferred embodiment of the invention. Among these, compositions which comprise at least one triazine herbicide also constitute a preferred embodiment of the invention. Among these, furthermore compositions which comprise at least one nitrile herbicide constititute a preferred embodiment of the invention;

b4) from the group of protoporphyrinogen IX oxidase inhibitors:

these are compounds whose herbicidal effect is based on the inhibition of protoporphyrinogen IX oxidase. Such inhibitors belong to group E of the HRAC classification. Examples are:

acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, sulfentrazone, thidiazimin, 2-chloro-5-[3,6-dihydro-3-methyl-2,6-dioxo-4-(trifluoromethyl)-1(2H-pyrimidinyl]-4-fluoro-N-[(isopropyl)methyl-sulfamoyl]benzamide (CAS 372137-35-4), ethyl[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7) and N-tetrahydrofurfuryl-3-(2-chloro-6-fluoro-4-trifluoromethylphenoxy)-5-methyl-1H-pyrazole-1-carboxamide (CAS 45100-03-7);

b5) from the group of bleacher herbicides (also referred to as herbicides with bleaching properties):

these are compounds whose herbicidal effect is based on the inhibition of or intereference in the carotenoid biosynthesis. These include compounds which prevent the carotenoid biosynthesis by inhibiting the phytoene desaturase (so-called PDS inhibitors, class F1 of the HRAC classification), compounds which inhibit the 4-hydroxyphenylpyruvate dioxygenase (HPPD inhibitors, class F2 of the HRAC classification), and also compounds which inhibit the carotenoid biosynthesis in an as yet unexplained manner (bleachers—unknown target, class F3 of the HRAC classification). Examples are:

PDS inhibitors: beflubutamid, diflufenican, fluridone, fluorochloridone, flurtamone, norflurazon, picolinafen and 4-(3-trifluoromethylphenoxy)-2-(4-trifluoromethyl-phenyl)pyrimidine (CAS 180608-33-7), HPPD inhibitors: benzobicyclon, benzofenap, isoxaflutole, mesotrione, pyrasulfotole, pyrazolynate, pyrazoxyfen, sulcotrione, tefuryltrione, tembotrione, topramezone, 4-hydroxy-3-[[2-[(2-methoxyethoxy)methyl]-6-(trifluoromethyl)-3-pyridyl]carbonyl]-bicyclo[3.2.1]oct-3-en-2-one (CAS 352010-68-5) and the compounds I described below which are different from those mentioned above, bleachers, unknown target: aclonifen, amitrol and clomazone;

b6) from the group of EPSP synthase inhibitors:

these are compounds whose herbicidal effect is based on the inhibition of the enolpyruvyl-shikimate-3-phosphate synthase and thus on the inhibition of the biosynthesis of amino acids in plants. Such inhibitors belong to group G of the HRAC classification. Examples are:

glyphosate, glyphosate-isopropylammonium and glyphosate-trimesium (sulfosate);

b7) from the group of glutamine synthase inhibitors:

these are compounds whose herbicidal effect is based on the inhibition of glutamine synthetase and is thus likewise based on the inhibition of the biosynthesis of amino acids in plants. Such inhibitors belong to group H of the HRAC classification. Examples are:

bilanaphos (bialaphos), bilanaphos-sodium, glufosinate and glufosinate-ammonium;

b8) from the group of DHP synthase inhibitors:

these are compounds whose herbicidal effect is based on the inhibition of 7,8-dihydropteroate synthase. Such inhibitors belong to group I of the HRAC classification. One example is:

asulam;

b9) from the group of mitosis inhibitors:

these are compounds whose herbicidal effect is based on the interference in or inhibition of the production or organization of microtubuli and thus inhibits mitosis. Such inhibitors belong to groups K1 and K2 of the HRAC classification. Among these, compounds of group K1, in particular dinitroanilines, are preferred. Examples are:

compounds of group K1: dinitroanilines such as benfluralin, butralin, dinitramine, ethalfluralin, fluchloralin, oryzalin, pendimethalin, prodiamine and trifluralin, phosphorus amidates such as amiprophos, amiprophos-methyl and butamiphos, benzoic acids such as chlorthal, chlorthal-dimethyl, pyridines such as dithiopyr and thiazopyr, benzamides such as propyzamide and tebutam, compounds of group K2: chlorpropham, propham and carbethamide.

Among these, compounds of group. K1 and in particular dinitroanilines are preferred;

b10) from the group of VLCFA inhibitors:

these are compounds whose herbicidal effect is based on the inhibition of the synthesis of long-chain fatty acids and thus on the interference in or inhibition of cell division in plants. Such inhibitors belong to group K3 of the HRAC classification. Examples are:

chloroacetamides such as acetochlor, alachlor, butachlor, dimethachlor, dimethanamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamide, naproanilide and napropamide, tetrazolinones such as fentrazamide, and others such as anilofos, cafenstrol, piperophos, pyroxasulfone and isoxazoline compounds of formula II different from pyroxasulfone

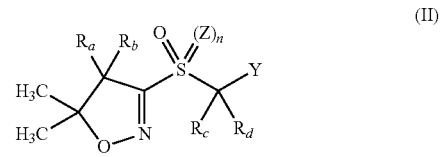

(II)

where $R_a$, $R_b$, $R_c$, $R_d$, Z, Y and n have the following meanings:

$R_a$, $R_b$, $R_c$, $R_d$ in each case independently of one another are hydrogen, halogen or $C_1$-$C_4$-alkyl;

Y is phenyl or monocyclic 5-, 6-, 7-, 8-, 9- or 10-membered heterocyclyl, comprising, besides carbon ring members, one, two or three identical or different heteroatoms selected from the group oxygen, sulfur or nitrogen as ring members, where phenyl and heterocyclyl are unsubstituted or carry 1, 2 or 3 substituents $R^{yy}$ which are selected from halogen, $C_1$-$C_4$-alkyl, $C_1$-$C_4$-alkoxy, $C_1$-$C_4$-haloalkyl or $C_1$-$C_4$-haloalkoxy, preferably phenyl or 5- or 6-membered aromatic heterocyclyl (hetaryl), which, besides carbon ring members, comprises one, two or three nitrogen atoms as ring members, where phenyl and hetaryl are unsubstituted or carry 1, 2 or 3 substituents $R^{yy}$, Z is oxygen or NH; and n is zero or one.

Among the isoxazoline compounds of formula II, preference is given to the isoxazoline compounds of formula II in which $R_a$, $R_b$, $R_c$, $R_d$ are in each case independently of one another H, F, Cl or methyl;

Z is oxygen;

n is 0 or 1; and

Y is phenyl, pyrazolyl or 1,2,3-triazolyl, where the three last-mentioned radicals are unsubstituted or carry one, two or three substituents $R^{yy}$, specifically one of the following radicals:

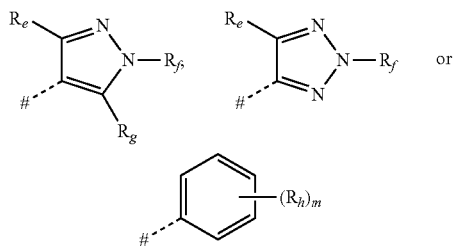

in which $R_e$ is halogen, $C_1$-$C_4$-alkyl or $C_1$-$C_4$-haloalkyl;
$R_f$ is $C_1$-$C_4$-alkyl;
$R_g$ is halogen, $C_1$-$C_4$-alkoxy or $C_1$-$C_4$-haloalkoxy;
$R_h$ is halogen, $C_1$-$C_4$-alkyl, $C_1$-$C_4$-haloalkyl or $C_1$-$C_4$-haloalkoxy;
m is 0, 1, 2 or 3; and
# indicates the linkage site to the group $CR_cR_d$.

Among these, very particular preference is given to isoxazoline compounds of formula II in which $R_a$ is hydrogen;
$R_b$ is fluorine;
$R_c$ is hydrogen or fluorine;
$R_d$ is hydrogen or fluorine;
Z is oxygen;
n is zero or 1, in particular 1; and
Y is one of the radicals of the formulae $Y_1$, $Y_2$, $Y_3$ or $Y_4$,

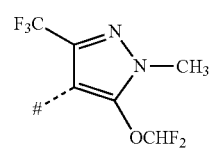

Y₁

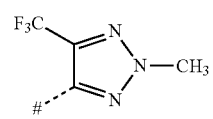

Y₂

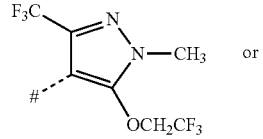

Y₃

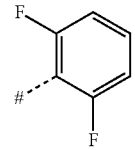

Y₄ in which # indicates the linkage site to the group $CR_cR_d$.

Among these, preference is given in particular to the isoxazoline compounds of the formulae II.1, II.2, II.3, II.4, II.5, II.6, II.7, II.8 and II.9.

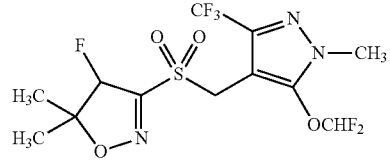

II.1

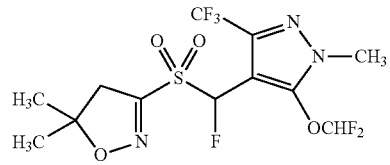

II.2

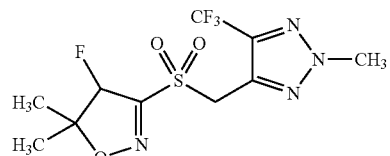

II.3

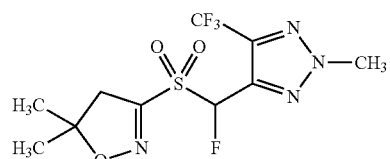

II.4

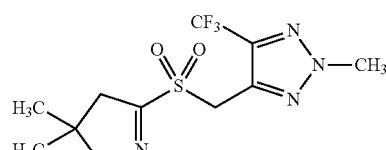

II.5

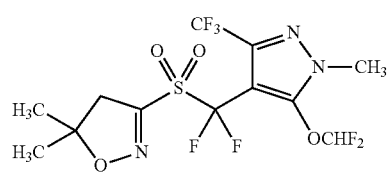

II.6

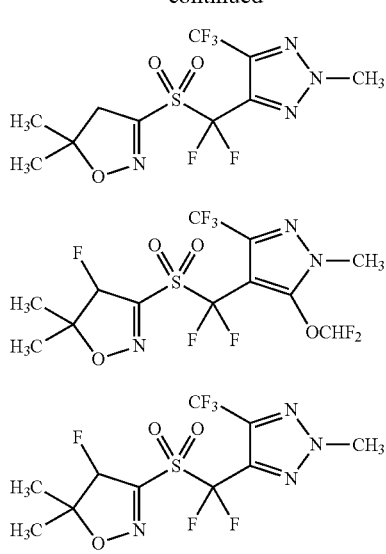

The isoxazoline compounds of formula II are known in the literature, e.g. from WO 2006/024820, WO 2006/037945, WO 2007/071900 and WO 2007/096576. Among the VLCFA inhibitors, chloroacetamides, oxyacetamides and pyroxasulfone are preferred;

b11) from the group of cellulose biosynthesis inhibitors:
these are compounds whose herbicidal effect is based on the inhibition of biosynthesis of cellulose and thus the formation of cell walls in plants. Such inhibitors belong to group L of the HRAC classification. Examples are:
chlorthiamide, dichlobenil, flupoxam and isoxaben;

b12) from the group of decoupler herbicides:
these are compounds whose herbicidal effect is based on the destruction of the cell membrane. Such inhibitors belong to group M of the HRAC classification. Examples are:
dinoseb, dinoterb and DNOC and its salts;

b13) from the group of auxin herbicides:
these are compounds which act like auxins, thus phytohormones in plants, and inhibit the growth of plants. Such substances belong to group O of the HRAC classification. Examples are:
2,4-D and its salts and esters, 2,4-DB and its salts and esters, aminopyralid and its salts such as aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluoroxypyr, fluoroxypyr-butomethyl, fluoroxypyr-meptyl, MCPA and its salts and esters, MCPA thioethyl, MCPB and its salts and esters, mecoprop and its salts and esters, mecoprop-P and its salts and esters and picloram and its salts and esters, quinclorac, quinmerac, TBA (2,3,6) and its salts and esters, triclopyr and its salts and esters, and 5,6-dichloro-2-cyclopropyl-4-pyrimidinecarboxylic acid (CAS 858956-08-8) and its salts and esters;

b14) from the group of auxin transport inhibitors:
these are compounds whose herbicidal effect is based on the inhibition of auxin transport in plants. Such substances belong to group P of the HRAC classification. Examples are:
diflufenzopyr, diflufenzopyr-sodium, naptalam and naptalam-sodium;

b15) from the group of other herbicides:
bromobutid, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, maleic hydrazide, mefluidide, metam, methyl azide, methyl bromide, methyl-dymron, methyl iodide, MSMA, oleic acid, oxaziclomefon, pelargonic acid, pyributicarb, quinoclamine, triaziflam, tridiphan and 6-chloro-3-(2-cyclopropyl-6-methylphenoxy)-4-pyridazinol (CAS 499223-49-3) and its salts and esters.

The herbicides B of groups b1) to b15) are known herbicides, see e.g. The Compendium of Pesticide Common Names (http://www.alanwood.net/pesticides/); Farm Chemicals Handbook 2000 Volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement to the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660. Further herbicidal active ingredients are known from WO 96/26202, WO 97/41116, WO 97/41117, WO 97/4111.8 and WO 01/83459 and from W. Kramer et al. (ed.) "Modern Crop Protection Compounds", Vol. 1, Wiley VCH, 2007 and the literature cited therein.

The assignment of the active ingredients to the particular action mechanisms is based on current knowledge. If two or more action mechanisms have an effect for an active ingredient, then this substance is only assigned one action mechanism.

If the herbicides B are able to form geometric isomers, e.g. E/Z isomers, it is possible to use either the pure isomers or their mixtures in the compositions according to the invention. If the herbicides B have one or more chirality centers and are thus present as enantiomers or diastereomers, then it is possible to use either the pure enantiomers and diastereomers or their mixtures in the compositions according to the invention.

If the herbicides B have ionizable functional groups, they can also be used in the form of their agriculturally compatible salts. In general, the salts of those cations or the acid addition salts of those acids are suitable whose cations, or anions, do not adversely affect the effect of the active ingredients. Suitable salts are described below in relation to compound I.

Those active ingredients B which have a carboxyl group can be used in the compositions according to the invention in the form of the acid, in the form of an agriculturally suitable salt, but also in the form of an agriculturally compatible derivative, e.g. as amides such as mono- and di-$C_1$-$C_6$-alkylamides or arylamides, as esters, e.g. as allyl esters, propargyl esters, $C_1$-$C_{10}$-alkyl esters, alkoxyalkyl esters and also as thioesters, e.g. as $C_1$-$C_{10}$-alkyl thioesters. Preferred mono- and di-$C_1$-$C_6$-alkylamides are the methyl- and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl)esters. Preferred $C_1$-$C_4$-alkoxy-$C_1$-$C_4$-alkyl esters are the straight-chain or branched $C_1$-$C_4$- alkoxyethyl esters, for example the methoxyethyl, ethoxyethyl or butoxyethyl esters. An example of the straight-chain or branched $C_1$-$C_{10}$-alkyl thioester is the ethyl thioester.

Preferably, the at least one herbicide is selected from herbicides with bleaching properties and particularly preferably from hydroxyphenylpyruvate dioxygenase inhibitors (HPPD inhibitors). Particularly preferably, the at least one herbicide is selected from HPPD inhibitors of the heterocycle type.

The HPPD inhibitors of the heterocycle type are here preferably selected from compounds of formula I

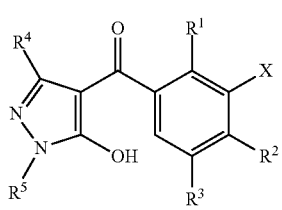

(I)

in which
R$^1$ and R$^2$, independently of one another, are hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl or $C_1$-$C_6$-haloalkylsulfonyl;
R$^3$ is hydrogen, halogen or $C_1$-$C_6$-alkyl;
R$^4$ is hydrogen or $C_1$-$C_6$-alkyl;
R$^5$ is $C_1$-$C_6$-alkyl; and
X is a 5-membered saturated, partially unsaturated or aromatic heterocycle with 1, 2 or 3 heteroatoms as ring members which are selected from O, S and N, where the heterocycle can carry 1, 2, 3 or 4 substituents which are selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio and $C_1$-$C_6$-haloalkylthio;
and the agriculturally compatible salts thereof.

The compounds I and methods for their preparation are known, for example from WO 00/53014 and the literature cited therein.

Suitable agriculturally compatible salts are primarily the salts of those cations or the acid addition salts of those acids whose cations or anions do not adversely affect the fungicidal effect of the compounds I. Thus, suitable cations are, in particular, the ions of the alkali metals, preferably sodium and potassium, of the alkaline earth metals, preferably calcium, magnesium and barium, and of the transition metals, preferably manganese, copper, zinc and iron, and also the ammonium ion, which if desired can carry one to four $C_1$-$C_4$-alkyl substituents and/or a phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium and sulfoxonium ions, preferably tri($C_1$-$C_4$-alkyl)sulfoxonium.

Anions of acid addition salts which can be used are primarily chloride, bromide, fluoride, hydrogensulfate, sulfate, dihydrogenphosphate, hydrogenphosphate, phosphate, nitrate, hydrogencarbonate, carbonate, hexafluorosilicate, hexafluorophosphate, benzoate, and the anions of $C_1$-$C_4$-alkanoic acids, preferably formate, acetate, propionate and butyrate. They can be formed by the reaction of I with an acid of the corresponding anion, preferably of hydrochloric acid, hydrobromic acid, sulfuric acid, phosphoric acid or nitric acid.

Preferably, in compounds of formula I, R$^1$ and R$^2$, independently of one another, are halogen, $C_1$-$C_6$-alkyl, $C_1$-$C_6$-alkylthio, $C_1$-$C_6$-alkylsulfinyl or $C_1$-$C_6$-alkylsulfonyl, particularly preferably chlorine, methyl, ethyl, methylthio, methylsulfinyl or methylsulfonyl. R$^1$ is particularly preferably halogen or $C_1$-$C_6$-alkyl, more preferably halogen or $C_1$-$C_4$-alkyl, in particular chlorine, methyl or ethyl and specifically chlorine or methyl. R$^2$ is particularly preferably $C_1$-$C_6$-alkylthio, $C_1$-$C_6$-alkylsulfinyl or $C_1$-$C_6$-alkylsulfonyl, particularly preferably methylthio, methylsulfinyl or methylsulfonyl and specifically methylsulfonyl.

R$^3$ is preferably hydrogen or methyl and in particular hydrogen.

R$^4$ is preferably hydrogen, methyl or trifluoromethyl and in particular hydrogen.

R$^5$ is preferably $C_1$-$C_4$-alkyl, particularly preferably methyl, ethyl, isopropyl or isobutyl and specifically methyl.

X is preferably selected from isoxazolyl, 4,5-dihydroisoxazolyl and thiazolyl, which can carry 1, 2 or 3 substituents which are selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio and $C_1$-$C_6$-haloalkylthio. X is particularly preferably selected from isoxazolyl and 4,5-dihydroisoxazolyl which may be substituted by 1 or 2 $C_1$-$C_6$-alkyl groups. In particular, X is 4,5-dihydroisoxazolyl which can be substituted by 1 or 2 $C_1$-$C_6$-alkyl groups, and specifically is unsubstituted 4,5-dihydroisoxazolyl.

Preferred compounds I are listed in the table below:

| No. | R$^1$ | R$^2$ | R$^3$ | R$^4$ | R$^5$ | X |
|---|---|---|---|---|---|---|
| 1. | Cl | SO$_2$CH$_3$ | H | CH$_3$ | CH$_3$ | 2-Thiazolyl |
| 2. | Cl | SO$_2$CH$_3$ | H | H | CH$_3$ | 2-Thiazolyl |
| 3. | Cl | SO$_2$CH$_3$ | H | CH$_3$ | CH$_3$ | 4,5-Dihydroisoxazol-3-yl |
| 4. | Cl | Cl | H | CH$_3$ | CH$_3$ | 4,5-Dihydroisoxazol-3-yl |
| 5. | Cl | SO$_2$CH$_3$ | H | H | CH$_3$ | 4,5-Dihydroisoxazol-3-yl |
| 6. | Cl | SO$_2$CH$_3$ | H | H | CH$_3$ | 4,5-Dihydro-5-methylisoxazol-3-yl |
| 7. | Cl | SO$_2$CH$_3$ | H | H | CH$_3$ | 4,5-Dihydro-5,5-dimethylisoxazol-3-yl |
| 8. | Cl | SO$_2$CH$_3$ | H | H | CH$_3$ | 4,5-Dihydro-5-ethylisoxazol-3-yl |
| 9. | Cl | SO$_2$CH$_3$ | H | H | CH$_3$ | 4,5-Dihydro-5,5-diethylisoxazol-3-yl |
| 10. | Cl | SO$_2$CH$_3$ | H | H | CH$_3$ | 4,5-Dihydro-5-chloromethylisoxazol-3-yl |
| 11. | Cl | SCH$_3$ | H | H | CH$_3$ | 4,5-Dihydroisoxazol-3-yl |
| 12. | Cl | SO$_2$CH$_3$ | H | H | CH$_3$ | 4,5-Dihydro-5-ethoxyisoxazol-3-yl |
| 13. | Cl | SO$_2$CH$_3$ | H | H | CH$_3$ | 4,5-Dihydro-5-methoxyisoxazol-3-yl |
| 14. | CH$_3$ | SO$_2$CH$_3$ | H | H | CH$_3$ | 4,5-Dihydroisoxazol-3-yl |
| 15. | Cl | SO$_2$CH$_3$ | H | H | CH$_3$ | 4,5-Dihydro-4,5-dimethylisoxazol-3-yl |
| 16. | Cl | SO$_2$CH$_3$ | H | H | CH$_3$ | 4,5-Dihydro-5-ethylthioisoxazol-3-yl |
| 17. | Cl | SO$_2$CH$_3$ | H | H | CH$_3$ | 4,5-Dihydro-5-trifluoromethylisoxazol-3-yl |
| 18. | SCH$_3$ | SCH$_3$ | H | H | CH$_3$ | 4,5-Dihydroisoxazol-3-yl |

-continued

| No. | $R^1$ | $R^2$ | $R^3$ | $R^4$ | $R^5$ | X |
|---|---|---|---|---|---|---|
| 19. | Cl | $SO_2CH_3$ | H | H | $C_2H_5$ | 2-Thiazolyl |
| 20. | Cl | $SO_2CH_3$ | H | H | $C_2H_5$ | 4,5-Dihydroisoxazol-3-yl |
| 21. | Cl | $SO_2CH_3$ | H | H | $C_2H_5$ | 4,5-Dihydro-5-methylisoxazol-3-yl |
| 22. | Cl | $SO_2CH_3$ | H | H | $C_2H_5$ | 4,5-Dihydro-5,5-dimethylisoxazol-3-yl |
| 23. | Cl | $SO_2CH_3$ | H | H | $C_2H_5$ | 4,5-Dihydro-5-ethylisoxazol-3-yl |
| 24. | Cl | $SO_2CH_3$ | H | H | $C_2H_5$ | 4,5-Dihydro-5,5-diethylisoxazol-3-yl |
| 25. | Cl | $SCH_3$ | H | H | $C_2H_5$ | 4,5-Dihydroisoxazol-3-yl |
| 26. | Cl | $SO_2CH_3$ | H | H | $C_2H_5$ | 4,5-Dihydro-5-chloromethylisoxazol-3-yl |
| 27. | Cl | $SO_2CH_3$ | H | H | $C_2H_5$ | 4,5-Dihydro-5-ethoxyisoxazol-3-yl |
| 28. | Cl | $SO_2CH_3$ | H | H | $C_2H_5$ | 4,5-Dihydro-4,5-dimethylisoxazol-3-yl |
| 29. | $CH_3$ | $SO_2CH_3$ | H | H | $C_2H_5$ | 4,5-Dihydroisoxazol-3-yl |
| 30. | Cl | $SO_2CH_3$ | H | H | $C_2H_5$ | 4,5-Dihydro-5-ethylthioisoxazol-3-yl |
| 31. | Cl | $SO_2CH_3$ | H | H | $C_2H_5$ | 4,5-Dihydro-5-trifluoromethylisoxazol-3-yl |
| 32. | $SCH_3$ | $SCH_3$ | H | H | $C_2H_5$ | 4,5-Dihydroisoxazol-3-yl |
| 33. | Cl | $SO_2CH_3$ | H | H | $i-C_4H_9$ | 4,5-Dihydroisoxazol-3-yl |
| 34. | Cl | $SO_2CH_3$ | H | H | $CH_3$ | 3-Methylisoxazol-5-yl |
| 35. | Cl | $SO_2CH_3$ | H | H | $C_2H_5$ | 3-Methylisoxazol-5-yl |
| 36. | $CH_3$ | $SO_2CH_3$ | H | H | $C_2H_5$ | 3-Methylisoxazol-5-yl |
| 37. | $CH_3$ | $SO_2CH_3$ | H | $CH_3$ | $CH_3$ | 4,5-Dihydroisoxazol-3-yl |
| 38. | $CH_3$ | Cl | H | $CH_3$ | $CH_3$ | 4,5-Dihydroisoxazol-3-yl |
| 39. | $CH_3$ | $SO_2CH_3$ | H | H | $CH_3$ | 4,5-Dihydro-5-methylisoxazol-3-yl |
| 40. | $CH_3$ | $SO_2CH_3$ | H | H | $CH_3$ | 4,5-Dihydro-5,5-dimethylisoxazol-3-yl |
| 41. | $CH_3$ | $SO_2CH_3$ | H | H | $CH_3$ | 4,5-Dihydro-5-ethylisoxazol-3-yl |
| 42. | $CH_3$ | $SO_2CH_3$ | H | H | $CH_3$ | 4,5-Dihydro-5,5-diethylisoxazol-3-yl |
| 43. | $CH_3$ | $SO_2CH_3$ | H | H | $CH_3$ | 4,5-Dihydroisoxazol-3-yl |
| 44. | $CH_3$ | $SO_2CH_3$ | H | H | $CH_3$ | 4,5-Dihydro-4,5-dimethylisoxazol-3-yl |
| 45. | $CH_3$ | Cl | H | H | $C_2H_5$ | 4,5-Dihydroisoxazol-3-yl |
| 46. | $CH_3$ | $SO_2CH_3$ | H | H | $C_2H_5$ | 4,5-Dihydro-5-methylisoxazol-3-yl |
| 47. | $CH_3$ | $SO_2CH_3$ | H | H | $C_2H_5$ | 4,5-Dihydro-5,5-dimethylisoxazol-3-yl |
| 48. | $CH_3$ | $SO_2CH_3$ | H | H | $C_2H_5$ | 4,5-Dihydro-5-ethylisoxazol-3-yl |
| 49. | $CH_3$ | $SO_2CH_3$ | H | H | $C_2H_5$ | 4,5-Dihydro-4,5-dimethylisoxazol-3-yl |
| 50. | $CH_3$ | $SO_2CH_3$ | H | H | $i-C_4H_9$ | 4,5-Dihydroisoxazol-3-yl |

$i-C_4H_9$: isobutyl

The compounds are very particularly preferably 4-[2-chloro-3-(4,5-dihydroisoxazol-3-yl)-4-methylsulfonylbenzoyl]-1-methyl-5-hydroxy-1H-pyrazole, 4-[2-methyl-3-(4,5-dihydroisoxazol-3-yl)-4-methylsulfonylbenzoyl]-1-methyl-5-hydroxy-1H-pyrazole, 4-[2-chloro-3-(3-methylisoxazol-5-yl)-4-methylsulfonylbenzoyl]-1-methyl-5-hydroxy-1H-pyrazole and/or agriculturally compatible salts thereof.

In the herbicidal agent according to the invention, the weight ratio of the composition of component A to the at least one herbicide of component B is preferably 1:200 to 200:1, particularly preferably 1:100 to 100:1, more preferably 1:20 to 100:1, even more preferably 1:10 to 100:1 and in particular 1:5 to 100:1.

As already explained, the individual components A and B of the herbicidal agent according to the invention can be formulated and packaged together or individually.

The farmer uses the herbicidal agent as a mixture or individual components thereof preferably for application in a spray tank. This means the herbicidal agent according to the invention is fed to the plants primarily by leaf spraying. Here, the application can take place e.g. with water as carrier by customary spraying techniques with spray liquor amounts of about 100 to 1000 l/ha (e.g. 300 to 400 l/ha). An application of the herbicidal agent in the so-called "low volume" and "ultra-low volume" methods, however, is just as possible as their application in the form of so-called microgranules.

For the leaf spraying, the herbicidal agent, if it is in the form of a mixture, is diluted with water, with further auxiliaries and additives optionally being added. However, the farmer can also only mix the individual components A and B of the herbicidal agent according to the invention in the spraying tank and optionally add further auxiliaries and additives (tank mix method).

In the tank mix method, the components A and B are mixed in the spraying tank and converted to the desired application concentration using water.

Preferably, the two components of the agent according to the invention are formulated separately and are only mixed in the spraying tank.

For better processing, further auxiliaries and additives can be added. Auxiliaries and additives which have proven successful are the following components: solvents, antifoams, buffer substances, thickeners, spreading agents, agents which promote compatibility.

Examples and brands of adjuvants and auxiliaries and additives are described, for example, in Farm Chemicals Handbook, 1997; Meister Publishing, 197 p. C10, chapter "adjuvant" or in Weed Control Manual, 1998, p. 86.

The herbicidal agent according to the invention controls undesired plant growth on uncultivated surfaces very well, particularly at high application rates. In cultures such as wheat, rice, corn, soya and cotton, it is effective against weeds and harmful grasses without notably damaging the cultivated plants. This effect arises primarily at low application rates.

Depending on the particular application method, the herbicidal agent can also be used in a further number of cultivated plants for eliminating undesired plants. The following cultures, for example, are contemplated: *Allium cepa, Ananas comosus, Arachis hypogaea, Asparagus officinalis, Beta vulgaris* spec. *altissima, Beta vulgaris* spec.

*rapa, Brassica napus* var. *napus, Brassica napus* var. *napobrassica, Brassica rapa* var. *silvestris, Camellia sinensis, Carthamus tinctorius, Caryailli Boinensis, Citrus limon, Citrus sinensis, Coffea arabica* (*Coffea canephora, Coffea liberica*), *Cucumis sativusi, Cynodon dactylon, Daucus carota, Elaeis guineensis, Fragaria vesca, Glycine max, Gossypium hirsutum,* (*Gossypium arboreum, Gossypium herbaceurn, Gossypium vitifolium*), *Helianthusannuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Tritium aestivum, Tritium durum, Vicia faba, Vitis vinifera* and *Zea mays.*

Moreover, the herbicidal agent can also be used in cultures which are tolerant to the effect of herbicides through cultivation including genetic methods. Moreover, the herbicidal agent can also be used in cultures which are tolerant to insects or fungal attack through cultivation including genetic methods.

The application of the herbicidal mixture can take place in the pre-emergence or in the post-emergence method. If the herbicidal agent is not very compatible for certain cultivated plants, then application techniques can be employed in which the herbicidal agent is sprayed using the spraying device such that the leaves of the sensitive cultivated plants are where possible not affected, whereas the herbicidal agent reaches the leaves of undesired plants growing underneath or the uncovered soil surface (post-directed, lay-by).

The herbicidal agent can be applied, for example, in the form of directly sprayable aqueous solutions, powders, suspensions, also high-percentage aqueous, oily or other suspensions or dispersions, emulsions, oil dispersions, pastes, dusting agents, sprinkling agents or granules by spraying, atomization, dusting, sprinkling or pouring.

The application forms are governed by the intended uses; in each case they should ensure as far as possible the finest distribution of the herbicidal agent according to the invention.

Suitable inert additives are essentially:
mineral oil fractions of average to high boiling point, such as kerosene or diesel oil, also coal tar oils and oils of vegetable or animal origin, aliphatic, cyclic and aromatic hydrocarbons, e.g. paraffin, tetrahydronaphthalene, alkylated naphthalenes or derivatives thereof, alkylated benzenes or derivatives thereof, alcohols such as methanol, ethanol, propanol, butanol or cyclohexanol, ketones such as cyclohexanone or strongly polar solvents, e.g. amines such as N-methylpyrrolidone or water.

Aqueous application forms can be prepared from emulsion concentrates, suspensions, pastes, wettable powders or water-dispersible granules by adding water. To prepare emulsions, pastes or oil dispersions, the herbicidal agent can be homogenized in water as it is or dissolved in an oil or solvent, by means of wetting agents, adhesives, dispersants or emulsifiers. However, it is also possible to produce concentrates consisting of effective substance, wetting agent, adhesive, dispersant or emulsifier and possibly solvent or oil which are suitable for dilution with water.

Suitable surface-active substances are the alkali metal salts, alkaline earth metal salts, ammonium salts of aromatic sulfonic acids, e.g. lignin-, phenol-, naphthalene- and dibutylnaphthalenesulfonic acid, and also of fatty acids, alkyl- and alkylarylsulfonates, alkyl-, lauryl ethers and fatty alcohol sulfates, and also salts of sulfated hexa-, hepta- and octadecanols and of fatty alcohol glycol ethers, condensation products of sulfonated naphthalene and its derivatives with formaldehyde, condensation products of naphthalene and of naphthalenesulfonic acids with phenol and formaldehyde, polyoxyethylene octyl phenol ether, ethoxylated isooctyl, octyl or nonylphenol, alkylphenyl, tributylphenyl polyglycol ether, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignosulfite spent liquors or methylcellulose.

Powders, sprinkling agents and dusting agents can be prepared by mixing or common grinding of the herbicidal agent with a solid carrier.

Granules, e.g. coating granules, impregnation granules or homogeneous granules, can be produced by binding the herbicidal agent to solid carriers. Solid carriers are mineral earths such as silicas, silica gels, silicates, talc, kaolin, limestone, lime, chalk, bolus, loess, clay, dolomite, diatomaceous earth, calcium sulfate and magnesium sulfate, magnesium oxide, ground plastics, fertilizers, such as ammonium sulfate, ammonium phosphate, ammonium nitrate, ureas and vegetable products such as corn meal, tree bark, wood flour and nut shell flour, cellulose powder or other solid carriers.

The concentrations of the herbicidal agent in the ready-to-use preparations can be varied within wide ranges. In general, the formulations comprise approximately from 0.001 to 98% by weight, preferably 0.01 to 95% by weight, of the herbicidal agent.

It may be of use to apply the herbicidal agent alone or together in combination with further crop protection compositions, for example with compositions for controlling pests or phytopathogenic fungi or bacteria or with growth-regulating active ingredient groups. Also of interest is the miscibility with mineral salt solutions which are used for overcoming nutritional and trace element deficiencies. Further additives such as nonphytotoxic oils and oil concentrates can also be added.

The invention further provides the use of the herbicidal agent according to the invention for controlling undesired plants. Moreover, the invention relates to a method of controlling undesired plant growth, in which component A and component B of the herbicidal agent according to the invention are applied together or separately, at the same time or in succession, to the undesired plant or its habitat.

The order in which components A and B are applied is of minor importance. It is merely essential that the composition A and the at least one herbicide B are present at the site of action at the same time, i.e. at the same time have contact with the plant to be controlled or are absorbed by this.

The booster composition according to the invention remains liquid at significantly lower temperatures than analogous booster compositions of the prior art. It can thus be handled without problems even at low outside temperatures and does not need to be heated prior to use. Its effect-improving action on herbicides used together with it is identical or even better compared to products of the prior art.

EXAMPLES

1.) Preparation of the Composition According to the Invention

By mixing the following components in the stated weight fractions, a composition 1 according to the invention was prepared:

Composition 1 (According to the Invention)

37.5% by weight of Edenor® Me Ti 05 from Cognis (a mixture of different fatty acid methyl esters; comprises >71% by weight of methyl esters of aliphatic $C_{18}$-carboxylic acids, where methyl oleate is present in at least 65% by weight, based on the total weight of the mixture)

22.5% by weight of Anionic surfactant (Lutensit® A-EP from BASF SE)

5% by weight of Oleic acid 0.03% by weight of Trimethylsiloxane antifoam ad 100% by weight of Solvesso® 150 or Solvesso® 150 ND from Exxon Mobile Europe For comparison, a composition with a considerably lower fraction of aliphatic $C_{18}$-carboxylic acids was prepared. This composition corresponds approximately to composition No. 6 in WO 00/53014.

Composition 2 (Comparison)

37.5% by weight of Stepan® C-65 from Stepan Company (a mixture of different fatty acid methyl esters; comprises 52% by weight of methyl esters of aliphatic $C_{18}$-carboxylic acids (primarily oleic acid) and 45% by weight of aliphatic $C_{16}$-carboxylic acids (primarily palmitic acid))

22.5% by weight of Anionic surfactant (Klearfac® AA-270 from BASF Corp.)

5% by weight of Oleic acid 0.03% by weight of Trimethylsiloxane antifoam ad 100% by weight of Aromatic® 150 from Exxon Mobile USA 2.) Behavior at Low Temperatures The precipitation behavior of the two compositions upon storage for 4 and 8 weeks at low temperatures was investigated. The results are shown in the table below.

|  | Composition 1 - appearance | Composition 2 - appearance |
|---|---|---|
| Storage time: 4 weeks at |  |  |
| +15° C. | Clear | Clear |
| +10° C. | Clear | Precipitate formation |
| +5° C. | Clear | Precipitate formation |
| 0° C. | Clear | Solid, beige |
| −5° C. | Clear | Solid, beige |
| Storage time: 8 weeks at |  |  |
| +15° C. | Clear | Clear |
| +10° C. | Clear | Precipitate formation |
| +5° C. | Clear | Precipitate formation |
| 0° C. | Clear | Solid, beige |
| −5° C. | Clear | Solid, beige |

In order to show that the precipitate formation is actually attributable to the composition of the alkyl ester, the products Edenor® Me Ti 05 and Stepan® C-65 were stored at low temperatures and investigated with regard to the formation of solid constituents. At the start of the experiments, both products were clear. The results are listed in the table below:

|  | Edenor® Me Ti 05 - appearance | Stepan® C-65 - appearance |
|---|---|---|
| Storage time: 1 week at |  |  |
| +20° C. | Clear | Clear |
| +15° C. | Clear | Solid |
| +10° C. | Clear | Solid |
| +5° C. | Clear | Solid |
| 0° C. | Clear | Solid |
| −5° C. | Clear | Solid |
| −10° C. | Flocculation | Solid |
| −15° C. | Solid | Solid |
| Storage time: 4 weeks at |  |  |
| +20° C. | Clear | Precipitate formation |
| +15° C. | Clear | Solid |
| +10° C. | Clear | Solid |
| +5° C. | Clear | Solid |
| 0° C. | Clear | Solid |
| −5° C. | Clear | Solid |
| −10° C. | Precipitate formation | Solid |
| −15° C. | Solid | Solid |

The solid formed at −15° C. and −10° C. in the product Edenor® ME Ti 05 redissolved within 6 days at 0° C. In the case of Stepan® C-65, this did not occur in any case.

The invention claimed is:

1. A composition comprising components (a), (b), (c), (d) and (e) in the following fractions:
    (a) 35 to 40% by weight, based on the total weight of the components (a), (b), (c), (d) and (e), of at least one methyl or ethyl ester of at least one aliphatic $C_{14}$-$C_{22}$-carboxylic acid, where the at least one carboxylic acid consists of at least 70% by weight of aliphatic carboxylic acids having 18 carbon atoms, where the aliphatic carboxylic acids having 18 carbon atoms of component (a) is a mixture of at least one saturated $C_{18}$-carboxylic acid, at least one monounsaturated $C_{18}$-carboxylic acid, at least one diunsaturated $C_{18}$-carboxylic acid and at least one triunsaturated $C_{18}$-carboxylic acid, where the amount of monounsaturated $C_{18}$-carboxylic acid is at least 60%, based on the total weight of this mixture, where the at least one monounsaturated $C_{18}$-carboxylic acid comprises oleic acid;
    (b) 20 to 25% by weight, based on the total weight of the components (a), (b), (c), (d) and (e), of at least one anionic surfactant which is selected from the esterification products of monohydroxy-functional alkyl polyethers with inorganic polyprotonic acids;
    (c) 3 to 7% by weight, based on the total weight of the components (a), (b), (c), (d) and (e), of at least one aliphatic $C_{14}$-$C_{22}$-carboxylic acid, where the fraction of oleic acid is at least 80%, based on the total weight $C_{14}$-$C_{22}$-carboxylic acid of component (c);
    (d) 0 to 0.5% by weight, based on the total weight of the components (a), (b), (c), (d) and (e), of optionally at least one antifoam; and
    (e) at least one aromatic solvent, 100% by weight, based on the total weight of components (a), (b), (c), (d) and (e).

2. The composition according to claim 1, where the at least one aliphatic $C_{14}$-$C_{22}$-carboxylic acid of component (a) consists of at least 80% by weight of aliphatic carboxylic acids having 18 carbon atoms.

3. The composition according to claim 1, where the methyl or ethyl ester of component (a) is a methyl ester.

4. The composition according to claim 1, where the at least one saturated $C_{18}$-carboxylic acid comprises stearic acid,
    where the at least one diunsaturated $C_{18}$-carboxylic acid comprises linoleic acid, and
    where the at least one triunsaturated $C_{18}$-carboxylic acid comprises linolenic acid and/or elaeostearic acid.

5. The composition according to claim 1, where the at least one anionic surfactant of component (b) is selected from phosphoric acid esters of at least one monohydroxy-functional alkyl polyether, and
where the at least one phosphoric acid ester of at least one monohydroxy-functional alkyl polyether is selected from phosphoric acid half-esters of at least one monohydroxy-functional alkyl polyether which are obtainable by oxyalkylation of $C_{10}$-$C_{30}$-alkanols with at least one $C_2$-$C_4$-alkylene oxide.

6. The composition according to claim 1, where the at least one aliphatic $C_{14}$-$C_{22}$-carboxylic acid of component (c) is oleic acid.

7. The composition according to claim 1, where the at least one aromatic solvent of component (e) comprises at most 1% by weight, based on the total weight of the aromatic solvent, of naphthalene.

8. A herbicidal agent comprising
(A) a composition according to claim 1; and
(B) at least one herbicide.

9. The herbicidal agent according to claim 8, where the at least one herbicide is selected from hydroxyphenylpyruvate dioxygenase (HPPD) inhibitors.

10. The herbicidal agent according to claim 9, where HPPD inhibitors of the heterocycle type are selected from compounds of the formula I

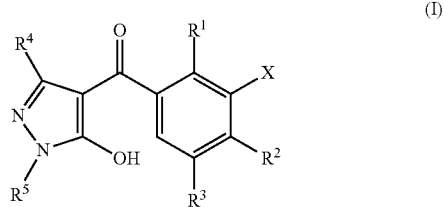

(I)

in which $R^1$ and $R^2$, indendently of one another, are hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl or $C_1$-$C_6$-haloalkylsulfonyl;

$R^3$ is hydrogen, halogen or $C_1$-$C_6$-alkyl;

$R^4$ is hydrogen or $C_1$-$C_6$-alkyl;

$R^5$ is $C_1$-$C_6$-alkyl; and

X is a 5-membered saturated, partially unsaturated or aromatic heterocycle with 1, 2 or 3 heteroatoms as ring members which are selected from O, S and N, where the heterocycle can carry 1, 2, 3 or 4 substituents which are selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio and $C_1$-$C_6$-haloalkylthio;

and the agriculturally compatible salts thereof.

11. The herbicidal agent according to claim 10, where $R^3$ is hydrogen, $R^i$ and $R^2$, independently of one another, are selected from halogen, $C_1$-$C_6$-alkyl, $C_1$-$C_6$-alkylthio, $C_1$-$C_6$-alkylsulfinyl and $C_1$-$C_6$-alkylsulfonyl and X is selected from isoxazolyl, 4,5-dihydroisoxazolyl and thiazolyl, which can carry 1, 2 or 3 substituents which are selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio and $C_1$-$C_6$-haloalkylthio.

12. The herbicidal agent according to claim 8, where the at least one herbicide is an ALS inhibitor from the group of imidazolinones.

13. The herbicidal agent according to claim 8, where the weight ratio of component A to component B is 1:200 to 200:1.

* * * * *

UNITED STATES PATENT AND TRADEMARK OFFICE
CERTIFICATE OF CORRECTION

PATENT NO. : 9,497,961 B2  
APPLICATION NO. : 13/121285  
DATED : November 22, 2016  
INVENTOR(S) : Michael Krapp et al.

Page 1 of 1

It is certified that error appears in the above-identified patent and that said Letters Patent is hereby corrected as shown below:

Column 26, Line 2, please delete the word "indendently" and replace it with "independently"

Signed and Sealed this
Thirteenth Day of June, 2017

Joseph Matal
*Performing the Functions and Duties of the
Under Secretary of Commerce for Intellectual Property and
Director of the United States Patent and Trademark Office*